Figure 1:
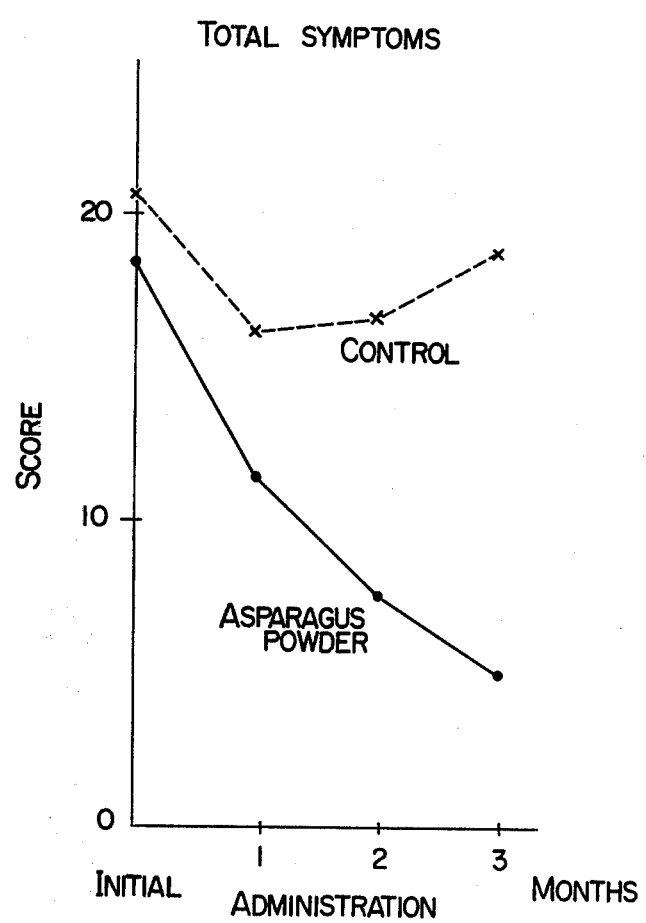

United States Patent [19]

Naito et al.

[11] 4,147,779

[45] Apr. 3, 1979

[54] METHOD FOR PREVENTING INTESTINAL DIVERTICULUM WITH EXPANDED FIBER BUNDLES OF ASPARAGUS

[75] Inventors: Ryoichi Naito, Ibaraki; Hirohisa Inahara, Kyoto; Satoru Shiino, Uji, all of Japan

[73] Assignee: The Green Cross Corporation, Osaka, Japan

[21] Appl. No.: 915,555

[22] Filed: Jun. 14, 1978

[30] Foreign Application Priority Data

Oct. 20, 1977 [JP] Japan .................................. 52-126245

[51] Int. Cl.$^2$ .............................................. A61K 35/78
[52] U.S. Cl. .................................................... 424/195
[58] Field of Search ......................................... 424/195

[56] References Cited

FOREIGN PATENT DOCUMENTS 51-42183  11/1976  Japan.

*Primary Examiner*—Donald B. Moyer
*Attorney, Agent, or Firm*—Cushman, Darby & Cushman

[57] ABSTRACT

A powder of expanded asparagus fiber bundles is obtained by keeping the integument of asparagus stems under a pressure of 2 to 8 kg/cm$^2$ (gage), then releasing the pressure in a moment, drying the spurted material, and pulverizing the dried material. This powder is used as a food additive for supplementing fibrous material to a diet deficient in vegetable fiber content and is effective in preventing acquired intestinal diverticulum.

1 Claim, 4 Drawing Figures

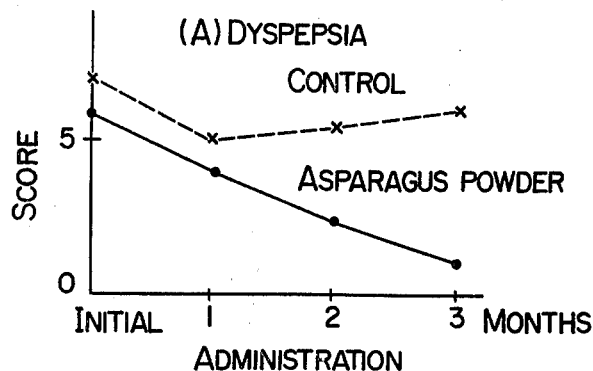
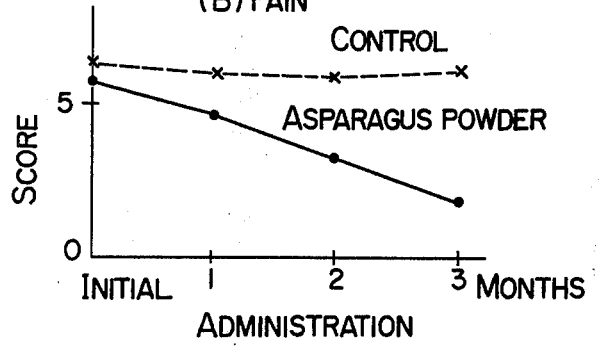
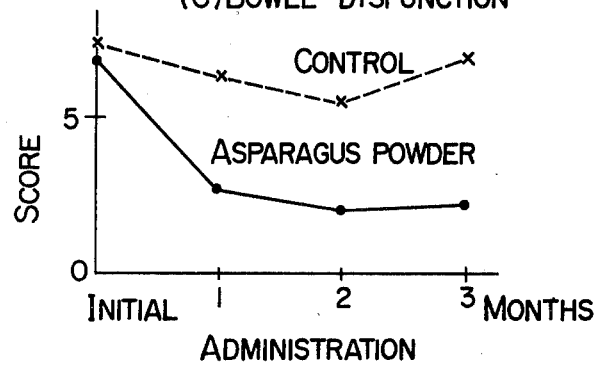

METHOD FOR PREVENTING INTESTINAL DIVERTICULUM WITH EXPANDED FIBER BUNDLES OF ASPARAGUS

This invention relates to a food additive comprising vegetable fibrous material, which is suitable for supplementing a diet defficient in fiber content.

One of the adult diseases which has recently attracted a special attention is intestinal diverticulum. It is acquired, a posteriori, frequently in the duodenum and the large intestine with symptoms generally resembling those of intestinal disease such as constipation, alternation of constipation and diarrhea, and abdominal pain. Further, if a patient suffers from diverticulitis due to bacterial infection of the intestive contents, he complains of not only abdominal pain but also fever, increased leucocyte count, nausea and vomitting. When the diverticulitis has aggravated, it is complicated by hemorrage, perforation, pericolonic abscess, fistula and obstruction which can be cured only by surgical treatments.

Further, a problem which has recently arisen is that the intestinal diverticulum can be associated with hyperlipemia and arteriosclerosis; the acquired intestinal diverticulum tends to elevate the concentrations of cholesterol and neutral lipids in the blood, thus leading to arteriosclerosis.

The results of extensive epidemiological investigations carried out in United States showed that the cause of acquired intestinal diverticulum is attributable to the deficiency in vegetable fibrous material in the diet. In Europe and America where people prefer foods rich in animal protein, about 5% of middle- and old-aged persons suffer from this disease; also in Japan morbidity of this disease is increasing year by year. Even though the cause of this disease has been elucidated, it is generally difficult for a person to change his own dietary habit.

The objects of this invention are to provide a food additive comprising vegetable fibrous material for use in preventing the acquired intestinal diverticulum and, in its turn, hyperlipemia and to provide a method for producing said additive.

In order to replenish the deficient vegetable fibrous material in one's diet without changing one's own dietary habit, it is desirable to use an additive comprising vegetable fibrous material as major component and not affecting the taste or odor or the feel of tongue. It is also desirable that the additive in a small amount is sufficient for the purpose. Moreover, the additive is required, of course, to be entirely free from side effects.

Based on the above consideration, the present inventors conducted an extensive investigation on the raw materials rich in vegetable fibrous matter (16% in fiber content on dry basis according to the "Standard Table for the Food Components, Japan") and as the result paid special attention to the integumentary layer of asparagus.

The central cylinder part of asparagus stem is used for food, whereas the integumentary part has heretofore been treated as waste because of its high content of difficultly digestible fibers. Therefore, the utilization of the waste part is desirable in industrial sense. However, when used in untreated form as a food additive to supplement a diet, the integment of asparagus stem poses various problems with respect to its form, properties, odor, taste, and storage life.

These problems are connected with the procedure for producing a dry fine powder. A dry powder may be obtained by boiling the sliced integument of the asparagus stem to remove thoroughly the soluble matter and then drying by customary procedures such as hot-air drying or drying by dry heating the material under application of pressure and then releasing the pressure in a moment. However, as compared with a powder obtained according to the procedure of this invention, the powder produced by the first-named customary procedure still retains a greater part of the original taste and odor and, in addition, feels harsh and extraneous to the tongue, while the powder produced by the second-named drying procedure has a disadvantage of carbonization.

According to the present invention, there is provided a food additive comprising expanded asparagus fiber bundles in powder form for supplementing fibrous material to a diet deficient in vegetable fiber content in order to prevent intestinal diverticulum.

In the accompanying drawings, FIGS. 1 to 4 show the results of therapeutic tests for diverticular diseases of human by administering a powder of expanded asparagus fiber bundles obtained according to the present invention, respectively.

The expanded fiber bundles in powder form provided by the present invention is produced by keeping the integumentary part of the asparagus stem under a pressure of 2 to 8 $kg/cm^2$ (gage), then releasing the pressure in a moment, thereafter drying and grinding the spurted material to collect a fine powder, the fibrous material deprived of bound water having been freed from taste and odor by washing with water.

The asparagus for use in this invention can be any species of the genus. Asparagus, though a common species for food use is preferable.

Although the whole stem of asparagus can be used, the integumentary part of the stem, which is a waste material resulting from the paring treatment of asparagus stem in preparing food, is preferred for the economical reason. The desirable raw materials are those removed of the bound water in the sense of food analysis rather than a fresh one containing the bound water. Such desirable materials are those which have been boiled or refined in water after boiling, or preserved with salt, or sealed in a container after having been flavored with water-soluble seasonings. Such materials are preferable because they are available throughout the year and are easily deodorized or treated to become tasteless. Fresh asparagus stems can, of course, be used.

The raw material is preferably subjected to a preliminary treatment of thorough washing with water to remove the soluble matter together with dirts and grits. This treatment is carried out preferably by using sliced stems. Subsequent to the washing treatment, the materials are preferably boiled for 6 to 10 hours to remove the impurities offensive to the taste. The material thus treated is subjected to the next pressure treatment either as such or after draining, the drained material being preferred.

The material treated preferably as mentioned above is placed in an autoclave and a heated steam is introduced into the autoclave to a pressure of 2 to 8 $kg/cm^2$ (gage). The material is kept under pressure for about 30 to 60 minutes at a temperature of 100° to 180° C. and then the pressure is released in a moment. During the heating, the steam in the autoclave can be in a saturated state or preferably in a superheated (dry) state which is maintained, if necessary, by heating through an external jacket to which heat is supplied by means of a heat medium or a superheated steam.

Depending upon the applied steam pressure, the material spurted together with the steam is disintegrated to a state ranging from a powder form to an approximately original form, mostly in a mixed form having an appearance of expanded fluff. After having been freed from the accompanying water by squeezing and, if necessary, washed with water to remove the water-soluble matter, the fluffy mass is dried at 70° to 80° C. in a current of air or preferably nitrogen or carbon dioxide. The dried material is ground to a powder by means of a pulverizer and preferably screened through a 42-mesh Tyler sieve to collect the fraction which has passed the sieve.

The tasteless and odorless powder thus obtained feels not extraneous to the tongue and swells easily on absorption of water. Microscopic examination reveals that the swollen powder in mostly composed of bundles of separate fibers. To the contrary, a powder prepared by sufficiently boiling the sliced pieces of the integument of asparagus stems, then washing with water and drying in a hot air current swells insufficiently in water and shows an appearance of simple block on microscopic examination. The powder of this invention has a composition comprising 0.5 to 5% of moisture, 1 to 5% of crude lipids, 10 to 20% of crude proteins, 20 to 50% of crude fiber, 20 to 50% of total saccharide and 0.5 to 2% of ash. It has a swelling degree (ml/100 ml) of 20 to 40 in each of the distilled water, artificial gastric juice (pH 6.2) and artificial intestinal juice.

The food additive of this invention is used by mixing in any way with a food deficient in fiber content. As a supplement to a food, it is used by cooking together with the food or mixing with a cooked food. It seems sufficient for the purpose of preventing intestinal diverticulum to add to every meal at least 0.5 g, preferably 0.5 to 2 g of the present additive. Alternatively, the present additive can be orally administered independent of food at every meal time in the form of powder, capsule, or tablet prepared by using the additive alone or in combination with customary auxiliaries.

The invention is illustrated below with reference to Examples. However, the invention is not limited to the Examples, since only such limitations should be imposed as are definitely indicated in the appended Claims.

EXAMPLE 1

About 40 kg of the stem integument of *asparagus officinalis Linn.* were transversally cut by means of a slicer into slices of a maximum thickness of 2 mm. The slices were placed in a vessel and sufficient water was added to cover the slices. They were boiled with heating three times each in fresh water, when the decoction became practically tasteless and odorless, indicating that a greater part of the components soluble in hot water had been extracted by the treatment. After having been drained, the boiled slices were placed in an autoclave. The water jacket directly connected with the autoclave was heated until a pressure of 3 kg/cm$^2$ (gage) was reached in the autoclave. After the internal pressure had been maintained for 30 minutes at this level, the autoclave was uncovered all at once. The spurted slices were collected in a receiver.

Owing to an abrupt change in pressure, the entire tissues of the slices had expanded, forming a product resembling fluff in appearance. The fluffy product was dried over a period of about 10 hours in a vacuum drier. The dried product was ground in a pulverizer and screened through a 42-mesh sieve to obtain 1,410 g of a powder, slightly yellowish in color. The powder was absolutely odorless. When put on the tongue, it developed neither perceptible taste nor extraneous feel to the tongue.

EXAMPLE 2

In a manner similar to that in Example 1, 10 kg of the slices prepared as in Example 1 were leached with boiling water. The treated slices were dehydrated by compression with an oil press. The dehydrated slices were placed in the same autoclave as used in Example 1. The pressure in the autoclave was elevated to 5 kg/cm$^2$ (gage) and maintained at this level for 10 minutes. The autoclave was then uncovered all at once to cause expansion of the tissue. The expanded slices were dried, ground, and screened to obtain 300 g of a powder. On organoleptic testing, the powder thus obtained was scarcely different from the powder of Example 1, except that the former was slightly superior to the latter in feel to the tongue.

EXAMPLE 3

In a manner similar to that in Example 1, 50 kg of the slices prepared as in Example 1 were leached with boiling water. The leached slices were dehydrated by compression with an oil press. The dehydrated slices were placed in the same autocalve as used in Example 1. The pressure in the autoclave was elevated to 8 kg/cm$^2$ (gage) and the autoclave was kept at 180° C. for 10 minutes. The autoclave was then uncovered all at once to cause expansion of the tissue of slices. The expanded slices were dried, ground, and screened to obtain 1,300 g of a powder. On organoleptic testing, the powder thus obtained was scarcely different from the powder of Example 2.

The uses of the powder of this invention are illustrated below with reference to examples.

USE EXAMPLE 1

To 250 ml of a soup prepared by using a commercial soup concentrate, was added 1.5 g of a powder obtained according to this invention. On eating, it was found that the incorporated powder did not affect the taste of soup at all and the soup was quite palatable as a light potage.

USE EXAMPLE 2

To a hamburg steak mixture comprising 400 g of finely chopped blend of beef and port, a half piece of onion which had been minced, one slice of bread, a small quantity of milk and one egg, was added 10 g of a powder of this invention. The resulting mixture was flavored with salt and nutmeg and then cooked. All of the members of a 10-membered taste evaluation group found the cooked steak to be satisfactorily palatable.

EXAMPLE 4 (Oral tablet)

A mixture was prepared from 300 g of the powder obtained in Example 1 containing 35% of crude saccharides, 14% of crude proteins, 2.8% of crude lipids, 40.6% of fibrous material, 0.94% of ash and 1.8% of water, and 50 g of calcium phosphate, 600 g of starch and 50 g of powdered gum arabic. After addition of water, the mixture was kneaded, formed into spherical granules and dried in vacuum to obtain granules, about 5 mm in diameter. The granules were compressed by means of a press to prepare tablets, each 500 mg in weight.

EXAMPLE 5 (oral capsule)

A mixture was prepared from 25 g of the same powder as used in Example 4, 15 g of corn starch, 9.8 g of cellulose and 0.2 g of magnesium stearate. Capsule shells were filled with each 300 mg of the above mixture to prepare capsules.

TEST EXAMPLE 1 (Acute toxicity test)

The powder obtained in Example 1 was tested for acute toxicity on test groups of male Wister rats, each group comprising five members weighing each 200 g. The powder was incorporated in a normal feed and orally administered at a dosage of 0.2 g/kg, 0.5 g/kg, 1 g/kg, 2 g/kg or 5 g/kg. No death case was recorded during seven days of observation. The test results confirmed that the safety level of the present powder is very high.

TEST EXAMPLE 2 (Animal test for efficacy)

As shown below, the results of experiments on the prevention of onset of atherosclerosis in the aorta of rabbit could confirm the efficacy of the present powder prepared from asparagus and containing fibrous material as active ingredient in replenishing a diet deficient in fiber content.

A ground of five male rabbits, each weighing about 3 kg, was given a synthetic feed which was deficient in fiber content and incorporated with 3% of cholesterol. Another group of five male rabbits was given a feed prepared by incorporating 3% by weight of the present powder derived from asparagus into the same feed as given to the above-noted group. After having been bred for 3 months, the rabbits were autopsied to cut open the aorta. In the first group atheroma was observed in the aorta in all cases, indicating the onset of atherosclerosis. To the contrary, in the second group which was given a feed containing the present powder, onset of atherosclerosis was observed in none of the cases and, moreover, both the cholesterol content and the neutral lipid content of the blood were lower than those in the first group fed with a feed not containing the present powder.

From the above experimental results, it is clearly seen that a food incorporated with the present powder can prevent hyperlipemia and artheriosclerosis, leading to the prevention of human intestinal diverticulum.

TEST EXAMPLE 3 (Therapeutic test for diverticular diseases of human)

1. Test methods.

(1) Patients.

Patients had large-bowel symptoms and the radiological changes of diverticular diseases, but no evidence of complications or other colonic disorders. They were receiving no treatment at the time.

(2) Test sample.

A wheat bread as test sample containing 15% by weight of the asparagus powder obtained in the same manner as in Example 1 was prepared by the usual manner. The asparagus powder used had a fiber content of 28% by weight.

(3) Administration.

Three slices of the test wheat bread (150 g) were supplied daily to each patient of one group (five patients) for three months. On the other hand, the same amount of wheat bread prepared from the same wheat as above containing no asparagus powder were supplied daily as control to each patient of another group (five patients) for three months. The patients were interviewed at monthly intervals to complete a symptomatic questionnaire on "dyspeptic" symptoms (nausea, vomiting, heart-burn, eructation, and abdominal distention), pain, and symptoms of "bowel dysfunction" (passage of excessive wind per rectum, the need to strain, the presence of anal pain on defecation, the frequency of evacuation, the consistency of the motion, the presence of blood or mucus, the feeling of incomplete emptying of the rectum after defecation, and the use of laxatives). Symptoms were scored 0–6 for frequency and severity on a standard descriptive scale, and the score for pain was doubled to give it the same weight to that of the other two symptoms. After the three months' treatment, their symptoms scores had been calculated.

2. Results.

The symptoms scores thus obtained are shown in the accompanying drawings. In the drawings, FIG. 1 shows the changes in mean symptom score over three months for the asparagus powder and control groups, for total symptoms, and FIG. 2 shows the changes in means symptom score over three months for the asparagus powder and control groups, for dyspepsia (A), FIG. 3 for pain (B) and FIG. 4 for bowel-dysfunction (C), respectively.

As is clear from the drawings, the therapeutic effect to decrease the symptoms by administering the asparagus powder obtained according to the present invention is significant as compared with the case where no asparagus powder is used.

What is claimed is:

1. A method for preventing intestinal diverticulum, which comprises adding to the diet at least 0.5 g per meal of a food additive comprising expanded fiber bundles of asparagus in powder form to supplement a fibrous component.

* * * * *